(12) United States Patent
Suzuki et al.

(10) Patent No.: US 8,258,351 B2
(45) Date of Patent: Sep. 4, 2012

(54) METHOD FOR PRODUCING HYDROGENOLYSIS PRODUCT OF POLYHYDRIC ALCOHOL

(75) Inventors: Nobuyoshi Suzuki, Wakayama (JP);
Masazumi Tamura, Wakayama (JP);
Taku Mimura, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/864,654

(22) PCT Filed: Dec. 26, 2008

(86) PCT No.: PCT/JP2008/073713
§ 371 (c)(1),
(2), (4) Date: Nov. 1, 2010

(87) PCT Pub. No.: WO2009/096134
PCT Pub. Date: Aug. 6, 2009

(65) Prior Publication Data
US 2011/0046418 A1    Feb. 24, 2011

(30) Foreign Application Priority Data
Jan. 30, 2008  (JP) .................. 2008-019819

(51) Int. Cl.
*C07C 29/00*    (2006.01)
(52) U.S. Cl. ....................... 568/852; 568/861
(58) Field of Classification Search .................. 568/852
See application file for complete search history.

(56) References Cited

U.S. PATENT DOCUMENTS 5,616,817 A    4/1997  Schuster et al.
2007/0149830 A1*  6/2007  Tuck et al. .................... 568/861

FOREIGN PATENT DOCUMENTS

JP    8-208541 A    8/1996
WO    WO 2007/010299 A1    1/2007

OTHER PUBLICATIONS

International Search Report issued in PCT/JP2008/073713, dated Feb. 3, 2009.

* cited by examiner

*Primary Examiner* — Sikarl Witherspoon
(74) *Attorney, Agent, or Firm* — Birch, Stewart, Kolasch & Birch, LLP

(57) ABSTRACT

The present invention relates to a process for producing a hydrogenolysis product of a polyhydric alcohol in the presence of a catalyst in which a conversion rate of the polyhydric alcohol as well as a selectivity to the hydrogenolysis product, in particular, a selectivity of glycerol to propanediols, can be enhanced. The process for producing a hydrogenolysis product of a polyhydric alcohol according to the present invention includes the step of subjecting a polyhydric alcohol solution having a water content of less than 10% by mass to hydrogenolysis by a fixed-bed continuous liquid phase reaction method in the presence of a hydrogenolysis catalyst.

5 Claims, 1 Drawing Sheet

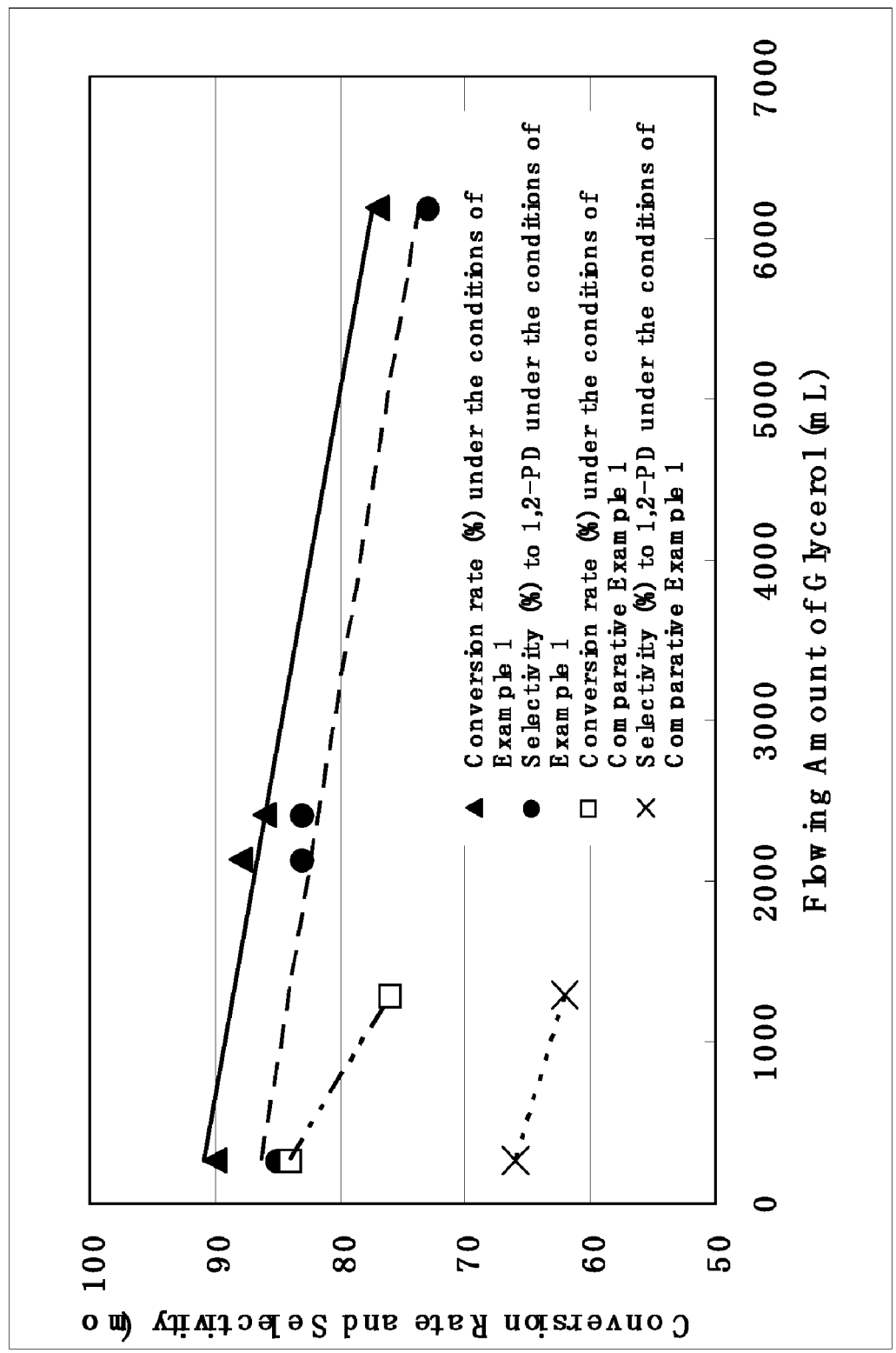

METHOD FOR PRODUCING HYDROGENOLYSIS PRODUCT OF POLYHYDRIC ALCOHOL

FIELD OF THE INVENTION

The present invention relates to a process for producing hydrogenolysis products of polyhydric alcohols with a high selectivity by converting the polyhydric alcohols into the aimed products in an efficient manner.

BACKGROUND OF THE INVENTION

Hydrogenolysis of polyhydric alcohols obtained from the natural world using a catalyst for converting the polyhydric alcohols into other compounds is an important technique from the viewpoint of effective utilization of materials or substances.

On the other hand, production of glycerol used as the polyhydric alcohol in food or medical applications has been increased year by year. One of the reasons therefor is the spread of bio-diesel fuels which have recently come to dominate owing to uncertain supply of fossil fuels or global warming problems. Glycerol is produced during the process for production of the bio-diesel fuels from raw vegetable materials. However, excessive supply of the glycerol has occurred due to currently limited applications thereof. Therefore, effective utilization of the glycerol has been demanded. As one solution of the above problem, a catalytic reaction of the glycerol for converting the glycerol into C3 alcohols has been noticed over the world.

The C3 alcohols are useful as various industrial materials, etc. Among the C3 alcohols, as diols, there are 1,3-propanediol and 1,2-propanediol. The 1,3-propanediol has been noticed as a raw material of polyesters and polyurethanes, etc.

On the other hand, the 1,2-propanediol has been used, for example, for production of polyester resins, paints, alkyd resins, various plasticizers, anti-freezing fluids, brake oils, etc., and further are useful for production of food wetting agents, viscosity increasers for fruit juices, cellophane softeners for food, cosmetics, drugs, etc.

In the circumstances, in order to effectively utilize glycerol, it has been considered to convert glycerol into propanediols, and there are therefore known various methods for producing 1,2-propanediol (hereinafter occasionally referred to merely as "1,2-PD") by hydrogenolysis of the glycerol.

For example, as the fixed-bed continuous liquid phase reaction methods, there are known (1) the method using a copper-chromium catalyst (for example, refer to Patent Document 1), (2) the method using a cobalt-copper-manganese-molybdenum catalyst (for example, refer to Patent Document 2), (3) the method using a copper-zinc-aluminum catalyst (for example, refer to Patent Document 3), (4) the method using a nickel-rhenium catalyst (for example, refer to Patent Document 4), (5) the method using a copper catalyst (for example, refer to Patent Document 5), etc.

In these fixed-bed continuous liquid phase reaction methods, a hydrogenation reaction may be generally carried out in a liquid phase using a solvent. As far as a hydrogenolysis of glycerol is concerned, in any of Patent Documents 1 to 5, water is used as the solvent. In these Patent Documents, there are described the reaction examples using water in an amount of 10% by mass or more. Specifically, in Patent Document 2, there is described the reaction example using water in an amount of 13.5% by mass or more, and in Patent Document 5, there is described the reaction example using water in an amount of 10% by mass or more. Incidentally, it is also described that in the fixed-bed continuous liquid phase methods (for example refer to Patent Document 6), the effect of protecting a catalyst is attained by using water as the solvent.

Patent Document 1: DP-A 4302464
Patent Document 2: EP-A 713849
Patent Document 3: EP-A 523015
Patent Document 4: PCT Pamphlet WO 03/035582
Patent Document 5: PCT Pamphlet WO 07/099,161
Patent Document 6: PCT Pamphlet WO 07/010,299

SUMMARY OF THE INVENTION

The present invention relates to a process for producing hydrogenolysis products of polyhydric alcohols using a catalyst which is enhanced in conversion rate of the polyhydric alcohols and selectivity to the aimed hydrogenolysis products.

As a result of extensive researches and studies concerning influences of addition of water on a catalyst in hydrogenolysis of polyhydric alcohols as raw materials by the fixed-bed continuous liquid phase reaction methods, the present inventors have found that no effect of protecting the catalyst by addition of water is recognized, and on the contrary, when no water is added, the catalyst has a long life and both the conversion rate and the selectivity can be enhanced.

Thus, the present invention relates to a process for producing a hydrogenolysis product of a polyhydric alcohol which includes the step of subjecting a polyhydric alcohol solution having a water content of less than 10% by mass to hydrogenolysis by a fixed-bed continuous liquid phase reaction method in the presence of a hydrogenolysis catalyst.

Meanwhile, the polyhydric alcohol solution as used in the present invention means a solution containing a polyhydric alcohol, and may also be the polyhydric alcohol itself which has a water content less than a predetermined value.

BRIEF DESCRIPTION OF THE DRAWING

FIG. 1 is a graph showing a reaction rate and a 1,2-PD selectivity relative to a flowing amount of glycerol.

DETAILED DESCRIPTION OF THE INVENTION

In the process for producing a hydrogenolysis product of a polyhydric alcohol according to the present invention, the polyhydric alcohol and hydrogen are heated in the presence of a catalyst to hydrogenolyze the polyhydric alcohol.

The polyhydric alcohol is preferably in the form of a compound having 2 to 6 hydroxyl groups. Examples of the polyhydric alcohol include aliphatic or alicyclic polyhydric alcohols having 2 to 60 carbon atoms. Specific examples of the polyhydric alcohol include various propanediols, various butanediols, various pentanediols, various pentanetriols, various hexanediols, various hexanetriols, glycerol, diglycerol, triglycerol, various cyclohexanediols, various cyclohexanetriols, pentaerythritol, trimethylol propane, and sugar alcohols such as sorbitol and mannitol. Among these polyhydric alcohols, from the viewpoint of construction of sustainable world, preferred are glycerol and sugar alcohols such as sorbitol and mannitol which are readily produced from biomasses such as sugars and oils and fats. Further, among these compounds, especially preferred is glycerol because the glycerol is present in an excessive amount and therefore inexpensive owing to the recent spread of bio-diesel fuels.

The hydrogenolysis product of the polyhydric alcohol as mentioned in the present invention means a compound obtained by reacting the polyhydric alcohol with hydrogen to decompose hydroxyl groups thereof to such an extent that at least one of the hydroxyl groups remains in a non-decomposed state. For example, the hydrogenolysis product of glycerol (number of hydroxyl groups in molecule: 3) includes a C3 diol (number of hydroxyl groups in molecule: 2) and a C3 monool (number of hydroxyl group in molecule: 1). Meanwhile, some of sugar alcohols such as sorbitol and mannitol may also undergo similar reactions via glycerol when they are subjected to hydrogenolysis.

As the above hydrogenolysis catalyst, there may be used solid catalysts or complex catalysts which are used for hydrogenation of unsaturated hydrocarbon compounds or carbonyl compounds such as alkenes, alkynes and aromatic compounds. Examples of the above hydrogenolysis catalyst include metals such as copper, nickel, cobalt, ruthenium, palladium, platinum and rhodium. Also, the hydrogenolysis catalyst may be in the form of a solid catalyst prepared by supporting any of these metals on a carrier. Among these catalysts, preferred are copper-containing catalysts, and especially preferred are copper/silica catalysts, copper-Raney catalysts and copper-iron-aluminum catalysts. The shape of a molded product obtained from these catalysts may be optionally determined unless the operation of a fixed-bed reactor used therefor is adversely affected. As the molded product of the catalyst, a catalyst precursor prepared by tableting or extrusion-molding the catalyst into a cylindrical shape, or a catalyst precursor prepared by forming the catalyst into spherical particles having a particle size of from 1 to 20 mm may be usually suitably used because these catalyst precursors can be readily produced at low costs. As the catalysts, there may also be used commercially available catalysts. Further, the catalyst used in the present invention may be a molded product which is prepared by first obtaining a catalyst powder by conventionally known methods such as, for example, a precipitation method, and then subjecting the thus obtained catalyst powder to extrusion-molding, etc.

The molded product of the catalyst may be reduced and activated by a vapor phase reduction method in which the reduction is carried out while flowing an inert gas containing hydrogen through the reaction system, or by a method in which the reduction is carried out by a hydrogen gas or an inert gas containing hydrogen while flowing a solvent through the reaction system.

In the present invention, the polyhydric alcohol solution to be reacted is preferably a solution of a polyhydric alcohol selected from the group consisting of glycerol, sorbitol and mannitol and most preferably a solution containing glycerol (hereinafter occasionally referred to merely as a "glycerol solution"). The present invention is characterized in that the content of water in the polyhydric alcohol solution is less than 10% by mass, preferably 5% by mass or less, more preferably 2% by mass or less and most preferably 1% by mass or less. The lower limit of the water content in the polyhydric alcohol solution is preferably 0.1% by mass or more, and more preferably 0.3% by mass or more. When the water content in the polyhydric alcohol solution is reduced, the reactivity of the polyhydric alcohol and the selectivity to the aimed product can be enhanced.

More specifically, the polyhydric alcohol solution as used in the present invention means a solution containing a polyhydric alcohol, and is especially preferably a polyhydric alcohol itself whose water content is less than a predetermined value.

The polyhydric alcohol solution used in the reaction of the present invention may also optionally contain an organic solvent such as methanol and ethanol which has no adverse influence on the reaction. However, in the present invention, in view of a good productivity, the reaction is desirably carried out in a solvent-free condition. Namely, the polyhydric alcohol solution is preferably a solution containing only a polyhydric alcohol and water.

In the present invention, from the industrial viewpoints, it is advantageous and preferable that after activating the catalyst in a fixed-bed continuous reactor by the above method, the polyhydric alcohol solution be subjected to hydrogenolysis reaction in the same reactor.

The reaction temperature is preferably from 130 to 300° C., more preferably from 180 to 250° C. and still more preferably from 210 to 230° C. The reaction pressure is preferably 0.1 MPa or more, more preferably 5 MPa or more, still more preferably 10 MPa or more, and further still more preferably 15 MPa or more. The upper limit of the reaction pressure is preferably 30 MPa or less, more preferably 27 MPa or less, still more preferably 22 MPa or less, and further still more preferably 20 MPa or less. The liquid hourly space velocity (LHSV; unit: $h^{-1}$) of the raw material fed may be optionally determined depending upon the reaction conditions. However, in view of a good productivity or a good reactivity, the LHSV is preferably in the range of from 0.1 to 5.0 $h^{-1}$ and more preferably from 0.2 to 1.0 $h^{-1}$. The hydrogenolysis of the present invention is carried out by contacting a hydrogen gas or a mixed gas of hydrogen and an inert gas with the catalyst precursor while feeding the gas to the reaction system. Examples of the inert gas usable for diluting hydrogen include nitrogen, helium, argon and methane. The feeding rate of hydrogen based on glycerol is controlled such that a molar ratio of $H_2$ to glycerol is from 1 to 100, preferably from 2 to 50 and more preferably from 3 to 30.

In the process for producing a hydrogenolysis product of a polyhydric alcohol according to the present invention, by using glycerol, sorbitol or mannitol, in particular, glycerol, as the polyhydric alcohol, it is possible to produce a hydrogenolysis product of the polyhydric alcohol, in particular, 1,2-PD, with a high conversion rate and a high selectivity in an efficient manner.

EXAMPLES

Example 1

A fixed-bed continuous reactor was charged with 26 g (30 mL) of a copper/silica catalyst (product number: "F01B"; a cylindrical extrusion-molded product; diameter: 1 mm; length: 2 to 8 mm; copper/silica ratio=1/0.55 (in terms of atomic ratio)) available from Nikki Chemical Co., Ltd. Next, a hydrogen gas (hydrogen concentration: 100%) was introduced into the reactor at a temperature of from 40 to 50° C. at a flow rate of 4.5 NL/h (gas hourly space velocity: 150 $h^{-1}$), and then lauryl alcohol (purity: 99.8%) was flowed through the reactor at a flow rate of 15 mL/h (liquid hourly space velocity: 0.5 $h^{-1}$).

After the flow rate of the gas introduced was stabilized, heating of the contents in the reactor was started at a temperature rise rate of 10° C./h under a hydrogen pressure of 2.0 MPa (gauge pressure). After the heating, the catalyst was subjected to reduction and activation treatment at 100° C. for 24 h.

Thereafter, lauryl alcohol was replaced with glycerol (purity: 99.7%; water content: 0.3%) at 80° C. over 24 h. Next, glycerol was introduced into the reactor at a liquid hourly space velocity of 0.5 $h^{-1}$ at 230° C. under a pressure of 2.0 MPa while flowing hydrogen therethrough in an amount of 5 mol per 1 mol of glycerol (gas hourly space velocity: 610 $h^{-1}$) to thereby subject the glycerol to hydrogenolysis reaction.

When 36 hours elapsed after initiation of the reaction, the reaction solution was sampled and analyzed by a gas chromatography under the following conditions to quantitatively determine the resulting products. As a result, it was confirmed that the products contained 1,2-propanediol, hydroxyacetone, ethylene glycol and other unknown substances. The results are shown in Table 1.

[Gas Chromatography]

Column: "Ultra-alloy capillary column", 15.0 m×250 μm×0.15 μm (available from Frontier Laboratories Inc.); Detector: FID; Injection temperature: 300° C.; Detector temperature: 350° C.; Flow rate of He: 4.6 mL/min

TABLE 1

|  |  | Examples |  |  |  |  |  |  |  |  |
|---|---|---|---|---|---|---|---|---|---|---|
|  |  | 1 | 2 | 3 | 4 | 5 | 6 | 7 | 8 | 9 |
| Water content in glycerol (mass %) |  | 0.3 | 0.3 | 0.3 | 0.3 | 0.3 | 0.3 | 0.3 | 0.3 | 0.3 |
| Feeding rate of glycerol (mol/h) |  | 0.2 | 0.12 | 0.2 | 0.2 | 0.2 | 0.2 | 0.12 | 0.12 | 0.2 |
| LHSV ($h^{-1}$) |  | 0.5 | 0.3 | 0.5 | 0.5 | 0.5 | 0.5 | 0.3 | 0.3 | 0.5 |
| $H_2$/glycerol: molar ratio |  | 5 | 5 | 10 | 15 | 25 | 15 | 15 | 25 | 25 |
| Pressure (MPa) |  | 2.0 | 2.0 | 2.0 | 2.0 | 2.0 | 2.0 | 2.0 | 2.0 | 20.0 |
| Reaction temperature (° C.) |  | 230 | 230 | 230 | 230 | 230 | 210 | 210 | 210 | 230 |
| Conversion rate of glycerol (mol %) |  | 90 | 95 | 98 | 99 | 99 | 82 | 76 | 94 | 83 |
| Selectivity (mol %) | 1,2-PD | 85 | 85 | 85 | 83 | 90 | 88 | 94 | 94 | 99 |
|  | Hydroxyacetone | 4 | 3 | 5 | 7 | 4 | 4 | 2 | 3 | 0 |
|  | Ethylene glycol | 3 | 3 | 2 | 2 | 2 | 2 | 2 | 1 | 1 |
|  | Others and unknown substances | 8 | 9 | 8 | 8 | 4 | 6 | 2 | 2 | 0 |

|  |  | Examples |  |  | Comparative Examples |  |  |  |
|---|---|---|---|---|---|---|---|---|
|  |  | 10 | 11 | 12 | 1 | 2 | 3 | 4 |
| Water content in glycerol (mass %) |  | 0.3 | 9 | 9 | 20 | 20 | 20 | 20 |
| Feeding rate of glycerol (mol/h) |  | 0.12 | 0.2 | 0.2 | 0.2 | 0.12 | 0.2 | 0.2 |
| LHSV ($h^{-1}$) |  | 0.3 | 0.55 | 0.55 | 0.68 | 0.38 | 0.68 | 0.68 |
| $H_2$/glycerol: molar ratio |  | 25 | 5 | 25 | 5 | 5 | 25 | 25 |
| Pressure (MPa) |  | 20.0 | 2.0 | 20.0 | 2.0 | 2.0 | 2.0 | 20.0 |
| Reaction temperature (° C.) |  | 210 | 230 | 230 | 230 | 230 | 230 | 230 |
| Conversion rate of glycerol (mol %) |  | 93 | 85 | 78 | 84 | 88 | 96 | 67 |
| Selectivity (mol %) | 1,2-PD | 99 | 72 | 99 | 66 | 67 | 74 | 98 |
|  | Hydroxyacetone | 0 | 8 | 0 | 11 | 7 | 10 | 0 |
|  | Ethylene glycol | 1 | 3 | 1 | 2 | 2 | 2 | 1 |
|  | Others and unknown substances | 0 | 17 | 0 | 21 | 24 | 14 | 1 |

Examples 2 to 10

The reaction was carried out under the conditions shown in Table 1 by using the same glycerol raw material as used in Example 1.

Examples 11 and 12

The reaction was carried out under the conditions shown in Table 1 by using a glycerol solution (glycerol content: 91% by mass; water content: 9% by mass) as a raw material.

Comparative Examples 1 to 4

The reaction was carried out under the conditions shown in Table 1 by using a glycerol solution (glycerol content: 80% by mass; water content: 20% by mass) as a raw material.

From the results of the above Examples and Comparative Examples, the followings were recognized. That is, from the comparison between Examples 1 and 11 and Comparative Example 1, between Example 2 and Comparative Example 2, between Example 5 and Comparative Example 3, and between Examples 9 and 12 and Comparative Example 4 which were respectively conducted at the same glycerol feeding rate under the same reaction conditions (including a $H_2$ molar ratio, a pressure and a reaction temperature), it was confirmed that the respective Examples were enhanced in both conversion rate and selectivity under the low-pressure condition (2.0 MPa), and further enhanced in conversion rate under the high-pressure condition (20.0 MPa).

Thus, when the glycerol having a less water content was used, the efficiency of production of 1,2-PD was enhanced.

In addition, in order to confirm the influence exerted on the catalyst by limiting a concentration of water in the raw material, the influences on the reactivity of glycerol and the selectivity to 1,2-PD relative to the flowing amount of glycerol were examined under the same conditions as used in Example 1 and Comparative Example 1, respectively. As a result, it was confirmed that under the conditions of Comparative Example 1, i.e., when using the glycerol solution (containing 80% by mass of glycerol and 20% by mass of water), the catalyst was deteriorated in its catalytic activity, and the reactivity of glycerol and the selectivity to 1,2-PD were deteriorated to a considerable extent. Therefore, since it was recognized that Comparative Example 1 was less practical, the procedure of Comparative Example 1 was terminated when the flowing amount of glycerol reached 1,300 mL and the reaction time reached 192 h. On the other hand, it was confirmed that when using the raw material containing substantially no water as used in Example 1, the catalyst was hardly deteriorated in its catalytic activity, and even after the flowing amount of glycerol reached 6,192 mL and the reaction time reached 876 h, the reactivity of glycerol and the selectivity to 1,2-PD were still kept in the practically acceptable ranges as high as 77% and 73%, respectively. The results are shown in FIG. 1.

From the above results, although it was conventionally mentioned that when using water or a mixture of water and a lower alcohol as a solvent in hydrogenolysis of glycerol, the water serves for not only reducing a viscosity of a material to be reacted but also protecting a catalyst used therein, it was actually recognized that as apparently shown in FIG. 1, the catalyst used in Example 1 using the glycerol raw material containing 0.3% by mass of water was hardly deteriorated in its catalytic activity as compared to the catalyst used in Comparative Example 1 using the glycerol raw material containing 20% by mass of water.

Industrial Applicability

The present invention can be suitably applied to a process for producing a hydrogenolysis product of a polyhydric alcohol by a fixed-bed continuous liquid phase reaction method using a hydrogenolysis catalyst and a polyhydric alcohol solution having a water content of less than 10% by mass, in particular, a process for producing 1,2-PD from glycerol with a high conversion rate and a high selectivity in an efficient manner.

The invention claimed is:

1. A process for producing a hydrogenolysis product of a polyhydric alcohol, comprising the step of subjecting a polyhydric alcohol solution having a water content of less than 10% by mass to hydrogenolysis by a fixed-bed continuous liquid phase reaction method in the presence of a hydrogenolysis catalyst.

2. The process for producing a hydrogenolysis product of a polyhydric alcohol according to claim 1, wherein the hydrogenolysis catalyst is a copper-containing catalyst.

3. The process for producing a hydrogenolysis product of a polyhydric alcohol according to claim 1 or 2, wherein the hydrogenolysis catalyst is a copper/silica catalyst.

4. The process for producing a hydrogenolysis product of a polyhydric alcohol according to claim 1, wherein the polyhydric alcohol is glycerol.

5. The process for producing a hydrogenolysis product of a polyhydric alcohol according to claim 4, wherein the hydrogenolysis product contains 1,2-propanediol as a main product.

* * * * *